(12) United States Patent
Patch

(10) Patent No.: US 6,173,030 B1
(45) Date of Patent: *Jan. 9, 2001

(54) ALMOST-EVERYWHERE EXTRAPOLATION USING 2D TRANSFORMS FROM CONE-BEAM DATA

(75) Inventor: Sarah Kathryn Patch, Saratoga Springs, NY (US)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/200,076

(22) Filed: Nov. 25, 1998

(51) Int. Cl.[7] .................................................... A61B 6/03

(52) U.S. Cl. .................................. 378/4; 378/15; 378/901

(58) Field of Search .................................. 378/4, 15, 901

(56) References Cited

U.S. PATENT DOCUMENTS

| | | | |
|---|---|---|---|
| 5,465,283 | 11/1995 | Tam | 378/4 |
| 6,009,142 | * 12/1999 | Sauer et al. | 378/15 |

OTHER PUBLICATIONS

Fritz John, "The Ultrahyperbolic Equation with 4 Independent Variables", Duke Math. Journal, pp. 300–322 (1938).

Leifur Asgeirsson, "Uber eine Mittelweretseigenschaft von Loesungen homogeneer linearer partieller Differentialgleichungen 2. Ordnung mit konstanten Koeffizienten", Mathematische Annalen, 13, pp. 321–346 (1938) with Englinsh language translation.

Glynn Owens, "An Explicit Formula for the Solution of the Ultrahyperbolic Equation in Four Variables", Duke Math Hournal, 9, pp. 272–282 (1942).

Glynn Owens "A Boundary–Value Problem for Analytic Solutions of an Ultrahyperbolic Equation", Duke Math Hournal, 20, pp. 29–38 (1953).

Copending U.S. Patent application Serial No. 09/113,841, filed Jul. 10, 1998, by S. Patch, entitled "Almost–Everywhere Extrapolation from Cone–Beam Data".

* cited by examiner

Primary Examiner—David V. Bruce
(74) Attorney, Agent, or Firm—Donald S. Ingraham; Douglas E. Stoner

(57) ABSTRACT

A source applies imaging energy that passes through an object being imaged and is then detected by a detector. A scanning trajectory causes the detector to provide measured cone beam data to a processor. The measured cone beam data is over a characteristic surface with a corresponding characteristic problem. The processor solves the characteristic problem such that missing cone beam data is determined. The measured cone beam data and the determined cone beam data together provide a complete data set for exact image reconstruction.

20 Claims, 4 Drawing Sheets

ALMOST-EVERYWHERE EXTRAPOLATION USING 2D TRANSFORMS FROM CONE-BEAM DATA

BACKGROUND OF THE INVENTION

This invention relates to X-ray imaging techniques, and, more particularly, to computerized tomography X-ray imaging using a minimal set of cone beam data measurements.

Computerized tomography (CT) uses a source of imaging energy such as X-ray energy and a detector for detecting imaging energy that has passed through an object of interest, often a patient being imaged for medical purposes. Typically, a single point source is used with an area detector such as an X-ray detector array.

Relative movement between the source, object of interest, and detector is used to collect data for image reconstruction purposes. Usually the source is moved, while the object and detector remain stationary relative to each other.

Typical source trajectories are "1 dimensional manifolds" described by parametric equations of a single variable. The advent of area X-ray detectors permits measurement of a 2 dimensional data set for each source position, since the detector lies in a 2 dimensional plane. Therefore, it is possible to measure a 1+2=3 dimensional data set of line integrals of the object being imaged.

This dimension count is encouraging for volummetric imaging such as CT because the imaged object lies in three spatial dimensions. More specifically, complete CT data for a family of parallel planes constitutes a 2+1=3 dimensional data set and completely determines the imaged object.

Unfortunately, cone beam data generated by a single point source does not permit simple reconstruction. A single circular trajectory does not provide a complete data set for Radon reconstruction (i.e., apart from measurement and discretization errors). Therefore, various scan trajectories have been used.

Among scan trajectories are two offset circular scans with a line extending between them.

Generally, the scan trajectories result from relative movement among the source, detector, and object being imaged. Usually, the source is moved in a path about the object to define the scan trajectory. The object being imaged is often a medical patient, but could also be an industrial part being imaged to locate possible defects. When the object being imaged is an industrial part, the scan trajectory may be defined at least partly by movement of the object relative to the source or relative to the detector. A scan trajectory might also be defined at least partly by movement of the detector.

Such scan trajectories that provide complete cone beam data may present a number of problems. The path or paths followed by the source or other component being moved may be complex. This requires a complex robotic function. Additionally, the scan time for obtaining a complete data set may be longer than desirable. Especially in the case where the imaged object is a patient, it is desirable to limit the time and dose of X-ray exposure. A complex scan path requires a longer time of exposure than a simple path. Yet, if the dose is reduced to partially compensate for a long exposure time, the signal to noise ratio is reduced. Errors in the data, particularly due to lag and signal to noise degradation with decreasing dose, often are more troublesome with complex scan paths. Further, a complex scan path increases the amount of measured data and this increase in data in turn increases computational demands when using the reconstruction process to provide an image.

Although it is possible to provide image reconstruction with a incomplete data set, such a reconstructed image will be quite inexact, if not undetermined, in some regions as a result of not having the missing data.

BRIEF SUMMARY OF THE INVENTION

In an exemplary embodiment of the method of the invention, an object is imaged by applying imaging energy from a source to the object. Imaging energy that has passed through the object is detected by a detector. The object is scanned with the imaging energy such that the detector collects measured image data of a "characteristic surface" corresponding to a "characteristic problem." "Characteristic surface," "characteristic problem" and the related "characteristic cone" are known mathematic concepts, but will also be defined in detail below. The characteristic problem is solved and the solution to the characteristic problem allows determination of a portion of the missing cone beam data. An image of the object is based on the measured image data and the determined missing cone beam data.

An exemplary embodiment of the system of the invention includes a source for applying imaging energy to the object. A detector detects imaging energy that has passed through the object. A positioner scans the object with the imaging energy such that the detector collects measured image data over a characteristic surface corresponding to a characteristic problem. An extrapolator extrapolates to solve the characteristic problem and determine missing cone beam data. An image supplier supplies an image of the object based on the measured image data and the determined missing cone beam data.

DETAILED DESCRIPTION OF THE INVENTION

Figure 1:
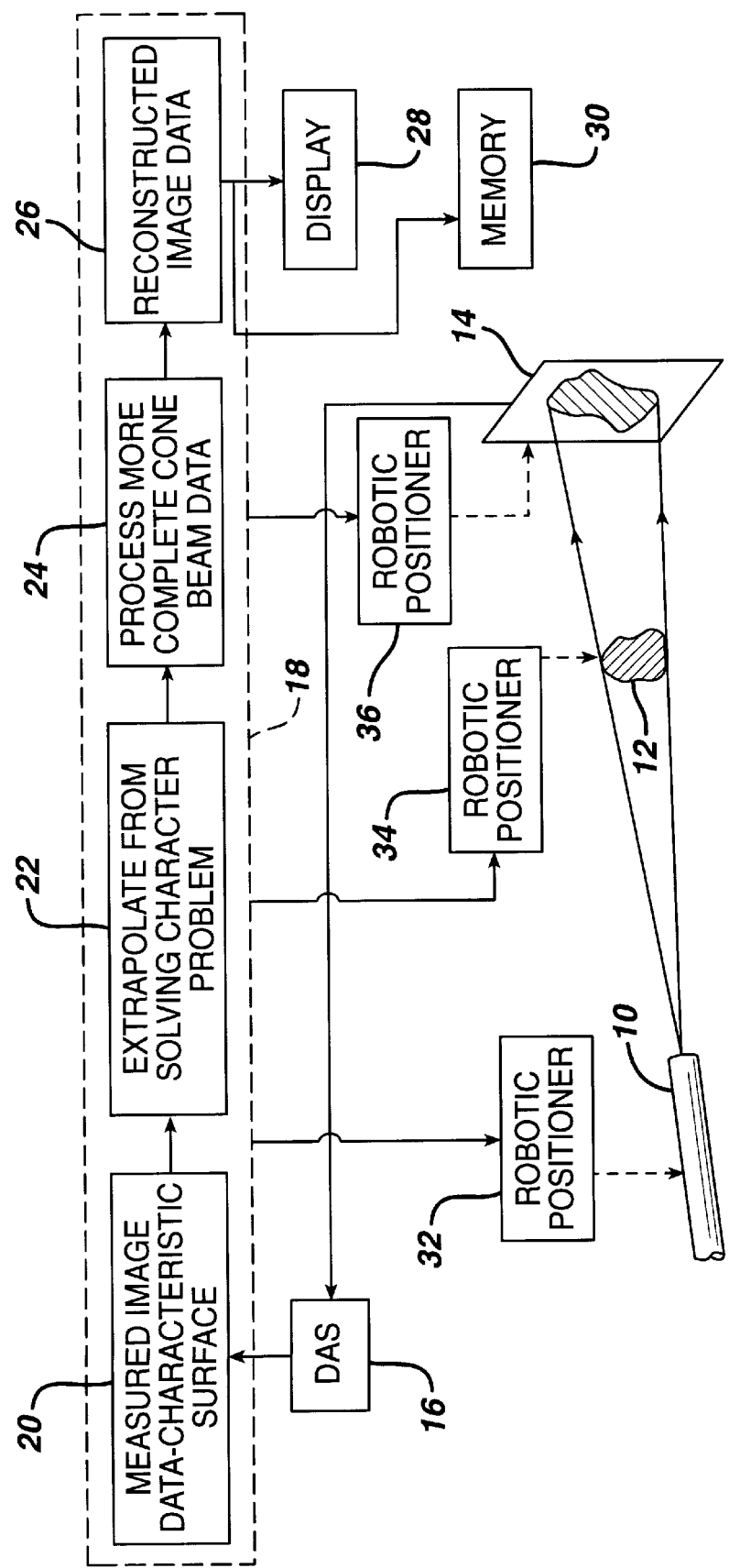
FIG. 1 is a simplified illustration of components of an imaging system and showing process steps within a processor.

Referring now to FIG. 1, imaging energy is applied by source 10 to object 12 and detected by detector 14. The source 10 typically comprises a cone beam X-ray source and the detector 14 typically comprises an area detector such as a two dimensional array detector having an array of individual detector elements (separate elements not shown). The object 12 typically comprises a patient (human or animal or tissue mass). Alternately, object 12 comprises an industrial part or other object being imaged using CT.

Cone beam energy that has passed through the object 12 is detected in detector 14 and converted to corresponding electrical signals and sent to a data acquisition unit 16 that registers the electrical signals. Unit 16 in turn sends cone beam data to a processor 18, which commonly comprises a computer programmed to perform various process steps.

Various process steps performed in processor 18 are shown in simplified form in FIG. 1. At block 20, the measured image data provided need not be a complete data set for image reconstruction, but provides complete characteristic boundary value data for John's equation. A characteristic surface is a term widely used in mathematics in connection with boundary value problems and satisfying certain criteria as discussed below. Once image data for a characteristic surface has been obtained, solving the characteristic problem, as explained in detail below, allows calculation of portions of missing cone beam data by extrapolation at block 22.

Although the measured data of block 20 and the portions of missing cone beam data determined at block 22 may not constitute a complete data set for exact reconstruction, their combination does permit fast reconstruction and image display, while preserving image quality compared to traditional reconstruction techniques. A "complete data set for exact reconstruction" as used herein means a data set providing image reconstruction accurate other than measurement errors and discretization errors. For example, measurement errors may arise from imprecision of the relative positioning of source and detector. Discretization errors can arise, for example, from basing measurements on the assumption that the source is at a plurality of discrete positions as it moves about its trajectory. If the measured cone-beam data is not complete, i.e. fails to satisfy the Kirillov-Tuy condition, extrapolated data will not complete the data set in terms of image reconstruction. However, extrapolation does permit conversion of the three-dimensional reconstruction problem into a family of simpler two dimensional reconstruction problems.

The portions of missing cone beam data that are determined are defined in detail below. This complete data set of cone beam data, some measured and some extrapolated, is supplied to block 24 for image reconstruction. For example, Radon derivative data is calculated followed by calculation of Radon data. Inverse Radon transformation is then typically performed to provide reconstructed image data at block 26. The processing of the complete cone beam data may be, for example, as disclosed in U.S. Pat. No. 5,465,283 of Tam, issued Nov. 7, 1998. Regardless of the particular image reconstruction process from cone beam data that is used, the block 26 supplies an image of the object (i.e., data corresponding to an image) that may be displayed by display 28, stored in a memory 30, or both.

The scanning trajectory will be defined by relative movements of the source 10, object 12, and detector 14 respectively controlled by robotic positioners 32, 34, and 36. Each of the robotic positioners 32, 34, and 36 causes relative scanning movement among the source 10, object 12, and detector 14. The positioners 32, 34, and 36 are in turn controlled by processor 18 to realize a scan trajectory satisfying criteria discussed below.

Although two or all three of the robotic positioners 32, 34, and 36 typically are part of the imaging system of FIG. 1, only one positioner is necessary in a given system. For example, the positioner 32 commonly is used in a single-positioner system to determine a scan trajectory by moving source 10 relative to object 12 and detector 14, both of which remain stationary.

Figure 2:
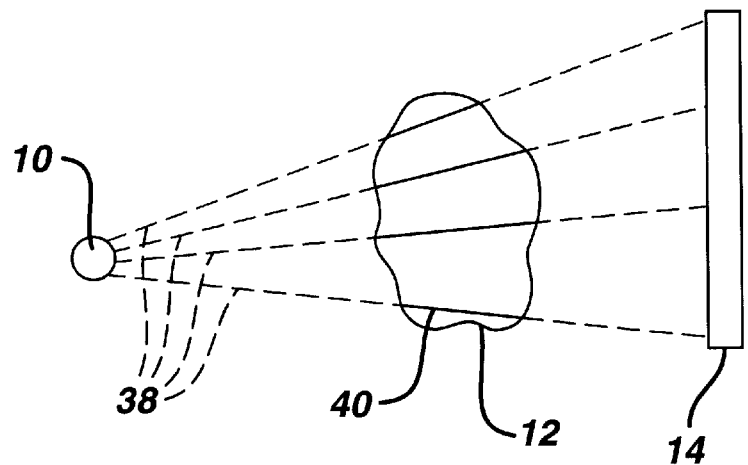
FIG. 2 is an illustration of some components of the imaging system and showing line integrals measured by the system.

FIG. 2 will be used to explain basic concepts used by the present invention before presenting more complex mathematical explanations. A source 10 is shown applying imaging energy beams 38 to pass through object 12 and strike the detector 14 (shown in side view). Four such energy beams 38 are shown for ease of illustration; the actual output of source 38 is a cone beam which may be considered as individual rays corresponding to the resolution of the area detector 14. In the simplified illustration, the detector 14 detects incident radiation corresponding to the four rays 38. Specifically, the data generated by detector 14 from the incident radiation is dependent on line integrals 40 representative of the extent to which rays 38 are attenuated by passing through object 12.

Figure 6:
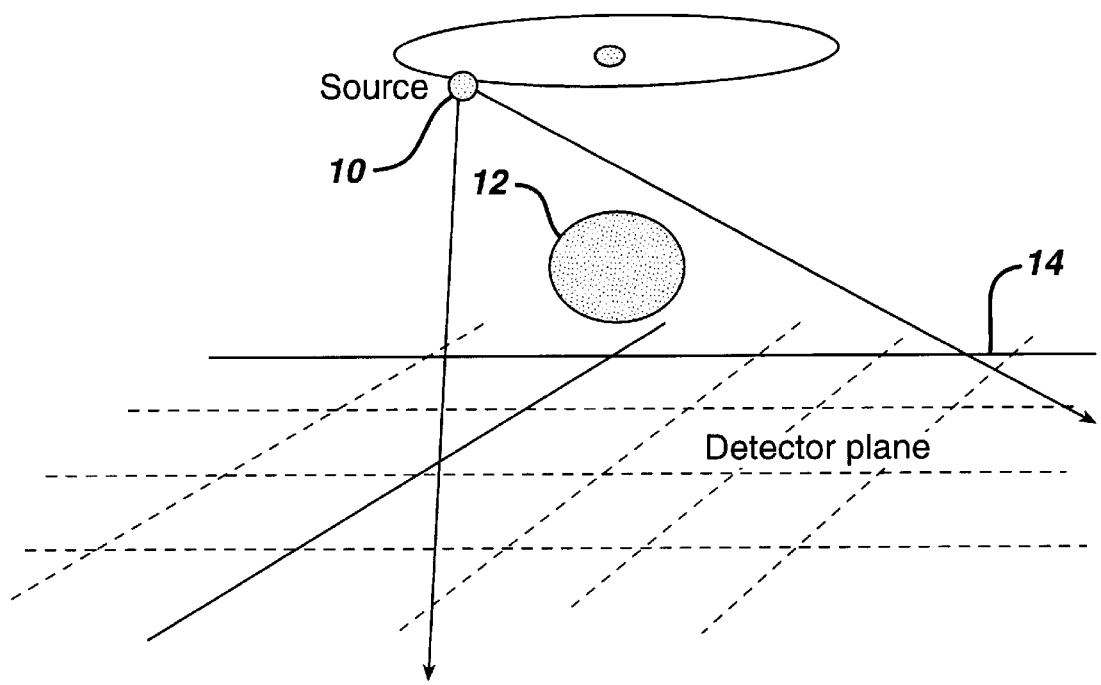
FIG. 6 is a simplified perspective view of the relationship of a source, imaged object, and detector plane.

One could measure a complete data set for exact reconstruction (i.e., providing a three dimensional image) by measuring a sufficient set of line integrals 40 as source 10 is scanned in a trajectory. However, present reconstruction techniques are either inexact or prohibitively slow. Furthermore, some clinical applications place constraints on gantry design that prohibit collection of a complete CT data set. For example, an open gantry system as depicted in FIG. 6 might be amenable to emergency room care, and must be adapted to allow for patient access by medical personnel. Unfortunately, this gantry design does not provide a mathematically complete volumetric CT data set. Even the incomplete data collected by such a system may provide image quality sufficient for medical diagnosis of serious injuries. In this example, quick reconstruction is vital for emergency room efficacy. Therefore, the advantage of this invention is in preprocessing the cone beam CT data to provide immediate image display.

The technique of the present invention obtains a data set corresponding to line integrals such as 40 which are necessary and sufficient for solution to a characteristic boundary value problem to John's equation. This "necessary and sufficient" terminology is used herein to represent that each measurement corresponds to a point on a characteristic surface, $\delta\Omega$, for John's equation and that for each point on the characteristic surface data has been measured. There is a one-to-one correspondence between points on the characteristic surface and measured data. Knowledge of measured data at all points on the characteristic surface is required for solution of John's equation in the characteristic cone; additional measurements are redundant in terms of solving John's equation for the characteristic surface $\delta\Omega$. This definition may be naturally extended to cases in which measurements corresponding to several different characteristic surfaces are combined to provide superior image quality. By eliminating collection of redundant data, a minimal amount of data for image reconstruction may thus be collected, reducing scan and reconstruction times. Also, this approach reduces the X-ray dose to a patient when the object being imaged is a patient. The present technique extrapolates CT data after collecting data over a characteristic surface. Two dimensional (2D) fast Fourier transforms are taken followed by solution of a first order transport equation. The source trajectory can be very simple and the method is stable numerically.

The present invention provides an alternate technique to the techniques described in the present inventor's prior U.S. application Ser. No. 09/113,841 filed Jul. 10, 1998 now U.S. Pat. No. 6,084,936, assigned to the assignee of the present application and entitled "ALMOST-EVERYWHERE EXTRAPOLATION FROM CONE-BEAM DATA." That application, which is hereby incorporated by reference, discloses an extrapolation technique using the solution to the Cauchy problem for John's equation.

The solution to a Cauchy problem requires that boundary value data, function values as well as derivatives, be prescribed on a noncharacteristic surface. Finding derivatives can introduce problems if the data are noisy. The present technique, however, permits solution with only function values (no derivatives) prescribed on a characteristic surface. This approach provides a technique for solving what is referred to as a "Goursat" problem.

Detailed Mathematics

Figure 3:
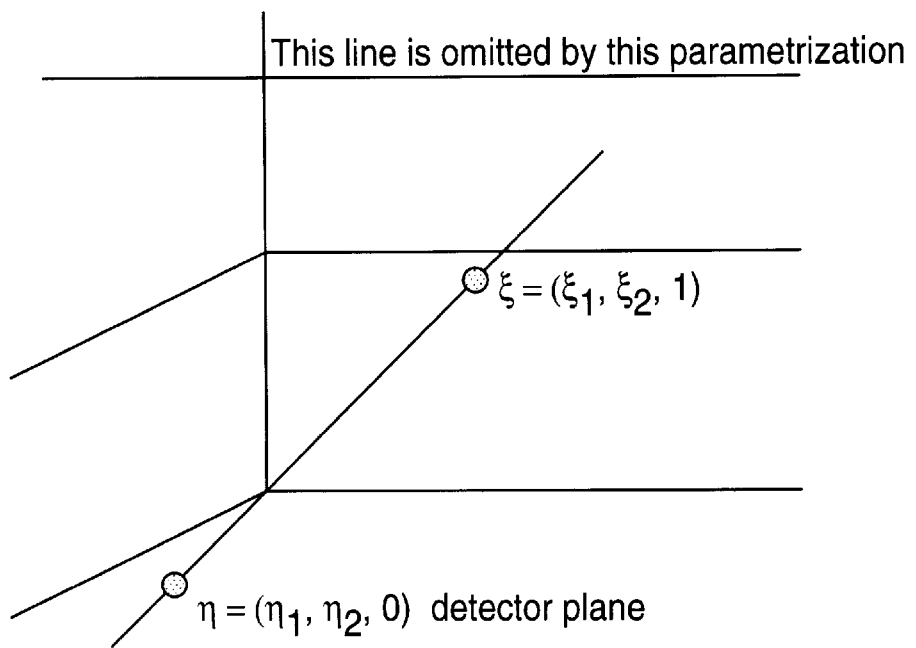
FIG. 3 shows a graph to illustrate mathematic concepts.

For simplicity of notation, and with reference to FIG. 3, a normalization function u is defined below:

$$u(\xi, \eta) = \frac{\chi_N \rho(\xi_1, \xi_2, 0; \eta_1, \eta_2, 1)}{\sqrt{(\xi_1 - \eta_1)^2 + (\xi_2 + \eta_2)^2 + 1}}$$

Where $\chi N \rho(\xi, \eta)$ denotes line integrals of $\rho$, the linear attenuation coefficient (LAC) of the imaged object, along the line through the points $\xi$ and $\eta$. See FIG. 3 where $\chi N \rho(\xi, \eta)$ integrates $\rho$ along the line passing through $\eta$ and $\xi$. Note that almost all lines except for horizontal lines can be parametrized by $\eta$ lying in the plane defined by $\{z=0\}$ and $\xi$ lying in the plane $\{z=1\}$. A single example of a line that cannot be parametrized is shown in FIG. 3 labeled as the line omitted by the parametrization. The map taking the LAC to its set of line integrals is underdetermined; the inversion taking a function's normalized line integrals to the function itself is overdetermined. This overdetermination manifests itself in the fact that a function's line integrals must satisfy John's equation:

$$\left(\frac{\partial^2}{\partial \xi_1 \partial \eta_2} - \frac{\partial^2}{\partial \xi_1 \partial \eta_2}\right) u(\xi_1, \xi_2; \eta_1, \eta_2) = 0 \quad (0.1)$$

Rather than solve the Cauchy problem to extrapolate data, the present technique uses a Fourier transform in two of the four variables, leaving a first order transport equation in the other two variables. Taking y as dual variable to $\eta$, where y, $\eta \in R^2$, the two dimensional real plane, $$\eta \sim y$$

The Fourier transform of John's equation with respect to $\eta$ results in a homogeneous transport equation for each y $$0 = \int_{R^2} \left(\frac{\partial^2}{\partial \xi_1 \partial \eta_2} - \frac{\partial^2}{\partial \xi_1 \partial \eta_2}\right) u(\xi; \eta) e^{2i\pi \eta \cdot y} d\eta \quad (0.2)$$

$$= -\int_{R^2} (2\pi i y_1 u_{\xi_2} - 2\pi i y_2 u_{\xi_1}) e^{2i\pi \eta \cdot y} d\eta \quad (0.3)$$

$$= (-2\pi i)(-y_2, y_1) \cdot \int_{R^2} (u_{\xi_1}, u_{\xi_2}) e^{2i\pi \eta \cdot y} d\eta \quad (0.4)$$

$$0 = y^{\perp} \cdot \nabla_{\xi} \hat{u}(\xi; y) \quad (0.5)$$

For example, data are collected along the source trajectory $$\xi_2 = 0$$

for each y one can compute from the measurement $\hat{u}(\xi, y)$ For each y such that $y \times (0,1) \neq 0$, $\hat{u}(\xi, y)$ is constant in $\xi$ along lines in direction $y_1$ (i.e., perpendicular to y)

$$\hat{u}(\xi; y) = \hat{u}(\xi + \tau y^{\perp}; y) \quad \forall \tau \in R^1 \quad (0.6)$$

$$= \hat{u}(\xi_1 + \xi_2 y_2 / y_1, 0; y) \quad (0.7)$$

To recover u one transforms back $$u(\xi; \eta) = \int_{R^2} \hat{u}(\xi; y) e^{2\pi i y \cdot \eta} dy \quad (0.8)$$

$$= \int_{R^2} \hat{u}(\xi_1 + \xi_2 y_2 / y_1, 0; y) e^{2\pi i y \cdot \eta} dy \quad (0.9)$$

Figure 4:
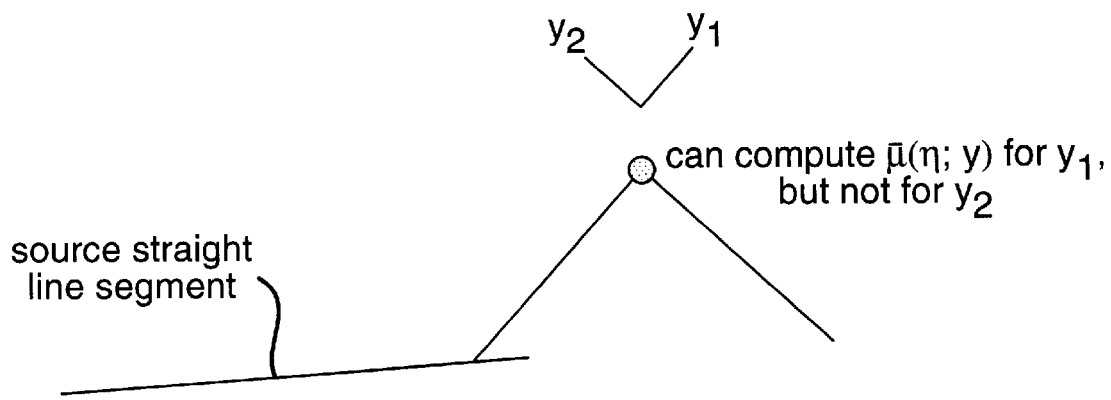
FIG. 4 shows the geometry of a limitation in computation ability for a particular source trajectory.

Even if the integrand in equation 0.9 were defined at the origin, in practice data cannot be collected along the entire line $\xi_2 = 0$. For any point, $\xi$, not on this line, there are some Fourier variables y for which one cannot solve the transport equation 0.5 because the characteristics do not intersect the line segment on which measurements are made. See FIG. 4 illustrating that, when the source moves along a straight line segment, one cannot compute the Fourier transform of u for y which do not have trajectories that hit the line segment. Of course, for points near the measurement line segment one can solve for most Fourier variables y.

Although the inverse Fourier transform cannot be computed exactly, the preferred method uses a circular source trajectory providing simple and exact extrapolation of data within the circle.

Figure 5:
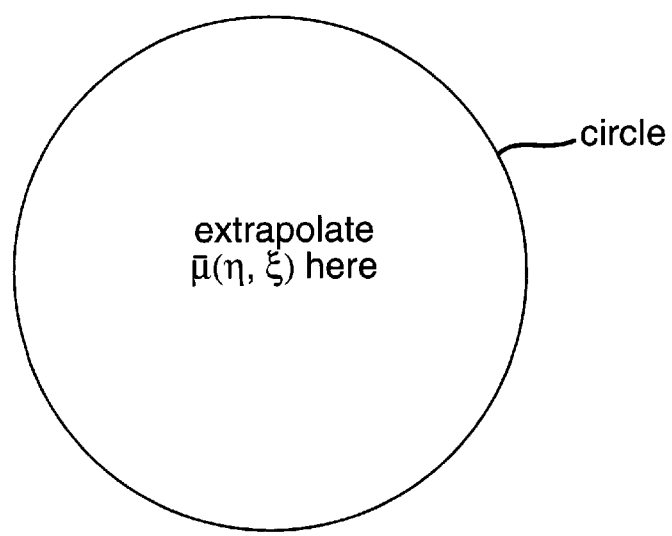
FIG. 5 is a planar view of a circular area corresponding to extrapolated data.

In one embodiment, the source 10 is moved along the trajectory $|\xi|=1$. Then for any point $(\xi; y)$ such that $|\xi|<1$, equation 0.7 allows completion of $u(\xi; \eta)$. The characteristic in direction $y_1$ intersect the circle of radius 1 at two points. See FIG. 5 showing a view of the plane in which the source trajectory lies. The source moves along a circular path. Extrapolated data are data that could have also been measured from source positions within the circular source trajectory. (Exact extrapolation cannot be performed outside the circle, although partial Fourier information can be recovered.) Note that data extrapolation is not predicated upon a circular source trajectory. Other source trajectories, such as helical trajectories, are alternatives. In the absence of any a priori information about the quality of estimates of $\hat{u}$ at these two points, $\rho_1$ and $\rho_2$, their values are averaged to estimate $u(\xi; \eta)$ $$\hat{u}(\xi; y) = \frac{1}{2}(\hat{u}(\rho_1; y) + \hat{u}(\rho_2; y)) \quad (0.10)$$

For each $\xi$ in the unit disc, there exists $\hat{u}(\xi, y) \forall y \in R^2$ and can therefore the method provides computation of the inverse Fourier transform with no difficulty.

The present technique uses data measurements on a characteristic surface. The symbol of a partial differential equation (PDE) is used to check whether a surface is characteristic. The symbol for John's equation is $$\Lambda(\xi, \eta) = \xi_1 \eta_2 - \xi_2 \eta_1 \quad (0.11)$$

If the function $\phi = \phi(\xi, \eta)$ defines the measurement surface $\delta \Omega$ a region $\Omega$, the condition for surface $\delta \Omega$ to be noncharacteristic is that $$\Lambda(\nabla \phi) \neq 0 \quad (0.12)$$

When $\phi_1 = 0 = \phi_2$ then $$\Lambda(\nabla \phi) \neq 0 \quad (0.13)$$

which means that the surface described by $\phi$ is characteristic. That surface is therefore a "characteristic surface" as that term is known in mathematics and used herein.

With reference to FIG. 6 showing the position of source 10, imaged object 12, and detector plane 14, the known mathematic concepts of "characteristic problem," "characteristic surface," and "characteristic cone" will be briefly explained. Solving the characteristic problem for John's equation allows determination of unmeasured cone beam data with the characteristic cone. For example, for the circular trajectory of source 10, data in the characteristic cone corresponds to all focal spot positions in the interior of the circular source trajectory. Only partial Fourier information about data corresponding to focal spot positions outside of the circle can be determined.

The technique gives a relatively quick and stable method for extrapolating cone beam CT data from a simple and practical source trajectory such as the circular source trajectory. Additional line integrals can be used to improve image quality, meaning that image resolution can be improved by taking additional measurements beyond a minimal data set.

This technique has a number of advantages over the prior art. The scanning time (data acquisition time) and reconstruction time can be reduced. Errors in the data, particularly due to lag and signal to noise degradation with decreasing dose, can be minimized. The amount of measured data is minimized and this reduces the computational demands for image reconstruction process steps.

While the invention has been described with reference to a preferred embodiment, it will be understood by those skilled in the art that various changes may be made and equivalents may be substituted for elements thereof without departing from the scope of the invention. In addition, many modification may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of imaging an object comprising the steps of:
   applying imaging energy from a source to the object;
   detecting imaging energy that has passed through the object by use of a detector;
   scanning the object with the imaging energy such that the detector collects measured image data on a characteristic surface corresponding to a characteristic problem for John's equation;
   solving the characteristic problem to determine missing cone beam data; and
   supplying an image of the object based on the measured image data and the missing cone beam data.

2. The method of claim 1 wherein the image of the object is an exact reconstruction of the object up to measurement and discretization errors.

3. The method of claim 2 wherein the measured image data and the determined missing cone beam data together constitute a complete data set for image reconstruction purposes.

4. The method of claim 3 wherein the detector is an area detector and the source is a point source.

5. The method of claim 4 wherein the scanning step is accomplished by moving the source in a scanning trajectory relative to the object.

6. The method of claim 4 wherein the scanning step is accomplished by moving the object in a scanning trajectory relative to the source.

7. The method of claim 4 wherein the scanning step uses a circular scanning trajectory and the missing cone beam data determined by the extrapolating step includes data corresponding to points interior to the circular scanning trajectory.

8. The method of claim 1 further including defining a normalization function u:

$$u(\xi, \eta) = \frac{X_N \rho(\xi_1, \xi_2, 0; \eta_1, \eta_2, 1)}{\sqrt{(\xi_1 - \eta_1)^2 + (\xi_2 + \eta_2)^2 + 1}}$$

where $\chi N\rho(\xi,\eta)$ denotes lines integrals of $\rho$, the linear attenuation coefficient (LAC) of the imaged object, along the line through the points $\xi=(\xi_1,\xi_2,0)$ corresponding to positions of the source and $\eta=(\eta_1,\eta_2,1)$ corresponding to the detector, where $\chi N\rho$ integrates $\rho$ along the line passing through $\eta$ and $\xi$; and wherein the solving of the characteristic problem includes applying a Fourier transform in two variables to John's equation:

$$\left(\frac{\partial^2}{\partial \xi_1 \partial \eta_2} - \frac{\partial^2}{\partial \xi_1 \partial \eta_2}\right) u(\xi_1, \xi_2; \eta_1, \eta_2) = 0.$$

9. The method of claim 8 wherein the solving of the characteristic problem includes taking y as dual variable to $\eta$, and where, after applying a Fourier transform in two variables, providing a transport equation for each y as follows:

$$0 = y^\perp \cdot \nabla_\xi \hat{u}(\xi; y)$$

and solving the transport equation.

10. The method of claim 9 wherein the scanning step is accomplished by moving the source in a circular scanning trajectory relative to the object.

11. A system for imaging an object comprising:
    a source of imaging energy;
    a detector;
    a positioner scanning the object with the imaging energy such that the detector collects measured image data for a characteristic surface corresponding to a characteristic problem for John's equation;
    an extrapolator extrapolating from the measured image data set to solve the characteristic problem and determine a portion of missing cone beam data; and
    an image supplier supplying an image of the object based on the measured image data and the determined missing cone beam data.

12. The system of claim 11 wherein the image of the object is an exact reconstruction of the object up to measurement and discretization errors.

13. The system of claim 12 wherein the measured image data and the determined missing cone beam data together constitute a complete data set for image reconstruction purposes.

14. The system of claim 13 wherein the detector comprises an area detector and the source comprises a point source.

15. The system of claim 14 wherein the positioner is adapted to dispose the source in a scanning trajectory relative to the object.

16. The system of claim 14 wherein the positioner is adapted to dispose the object in a scanning trajectory relative to the source.

17. The system of claim 14 wherein the positioner os adapted to provide a circular scanning trajectory and the extrapolator is configured to determine missing cone beam data including data corresponding to x-ray source points interior to the circular scanning trajectory.

18. The system of claim 11 wherein the extrapolator defines a normalization function u:

$$u(\xi, \eta) = \frac{X_N \rho(\xi_1, \xi_2, 0; \eta_1, \eta_2, 1)}{\sqrt{(\xi_1 - \eta_1)^2 + (\xi_2 + \eta_2)^2 + 1}}$$

where $X_N\rho(\xi;\eta)$ denotes lines integrals of $\rho$, the linear attenuation coefficient (LAC) of the imaged object, along the line through the points $\xi=(\xi_1,\xi_2,0)$ corresponding to positions of the source and $\eta=(\eta_1,\eta_2,1)$ corresponding to the detector, where $X_N\rho(\xi;\eta)$ integrates $\rho$ along the line passing through $\eta$ and $\xi$; and wherein the extrapolator solves of the characteristic problem by applying a Fourier transform in two variables to John's equation:

$$\left(\frac{\partial^2}{\partial \xi_1 \partial \eta_2} - \frac{\partial^2}{\partial \xi_1 \partial \eta_2}\right)u(\xi_1, \xi_2; \eta_1, \eta_2) = 0.$$

19. The system of claim 18 wherein the extrapolator solves the characteristic problem by taking y as dual variable to $\eta$, and where, after applying a Fourier transform in two variables, the extrapolator provides a transport equation for each y as follows:

$$0 = 2\pi i y^\perp \cdot \nabla_\xi \dot{u}(\xi;y)$$

and the extrapolator solves the transport equation.

20. The system of claim 19 wherein the positioner moves the source in a circular scanning trajectory relative to the object.

* * * * *